(12) United States Patent
Jiang et al.

(10) Patent No.: US 9,636,407 B2
(45) Date of Patent: May 2, 2017

(54) CASPOFUNGIN ACETATE FORMULATIONS

(71) Applicants: John Zhiqiang Jiang, Chicago, IL (US); Arunya Usayapant, Mundelein, IL (US); David Bowman, Mattawan, MI (US); Keith Kwok, Long Grove, IL (US); Joel Peterson, New Lenox, IL (US)

(72) Inventors: John Zhiqiang Jiang, Chicago, IL (US); Arunya Usayapant, Mundelein, IL (US); David Bowman, Mattawan, MI (US); Keith Kwok, Long Grove, IL (US); Joel Peterson, New Lenox, IL (US)

(73) Assignee: FRESENIUS KABI USA, LLC, Lake Zurich, IL (US)

(*) Notice: Subject to any disclaimer, the term of this patent is extended or adjusted under 35 U.S.C. 154(b) by 0 days.

(21) Appl. No.: 13/724,266

(22) Filed: Dec. 21, 2012

(65) Prior Publication Data

US 2014/0142032 A1    May 22, 2014

Related U.S. Application Data

(60) Provisional application No. 61/728,406, filed on Nov. 20, 2012.

(51) Int. Cl.
| | |
|---|---|
| *A61K 31/198* | (2006.01) |
| *A61K 47/18* | (2017.01) |
| *A61K 38/12* | (2006.01) |
| *A61K 9/19* | (2006.01) |
| *A61K 9/00* | (2006.01) |

(52) U.S. Cl.
CPC .......... *A61K 47/183* (2013.01); *A61K 9/0019* (2013.01); *A61K 9/19* (2013.01); *A61K 31/198* (2013.01); *A61K 38/12* (2013.01)

(58) Field of Classification Search
None
See application file for complete search history.

(56) References Cited

U.S. PATENT DOCUMENTS

| | | | | |
|---|---|---|---|---|
| 5,378,804 A | * | 1/1995 | Balkovec ................ | C07K 7/56 530/317 |
| 5,514,650 A | * | 5/1996 | Balkovec ................ | C07K 7/56 514/3.3 |
| 5,516,756 A | | 5/1996 | Balkovec et al. | |
| 5,552,521 A | | 9/1996 | Belyk et al. | |
| 5,668,105 A | | 9/1997 | Balkovec et al. | |
| 5,792,746 A | * | 8/1998 | Balkovec ................ | C07K 7/56 514/1.6 |
| 5,936,062 A | | 8/1999 | Leonard et al. | |
| 5,952,300 A | * | 9/1999 | Nerurkar et al. ............. | 514/3.3 |
| 6,803,046 B2 | | 10/2004 | Metcalfe et al. | |
| RE38,984 E | | 2/2006 | Abruzzo et al. | |
| 8,551,942 B2 | | 10/2013 | Mittal et al. | |
| 8,951,958 B2 | | 2/2015 | De Pater | |
| 9,056,897 B2 | | 6/2015 | De Pater et al. | |
| 9,321,779 B2 | | 4/2016 | Zhang et al. | |
| 9,393,307 B2 | | 7/2016 | Shirode et al. | |
| 9,394,340 B2 | | 7/2016 | Gurnani et al. | |
| 9,446,091 B2 | | 9/2016 | He et al. | |
| 2001/0038824 A1 | | 11/2001 | Horii et al. | |
| 2007/0116729 A1 | | 5/2007 | Palepu | |
| 2008/0108806 A1 | | 5/2008 | Keri et al. | |
| 2009/0170753 A1 | * | 7/2009 | Welz et al. ................... | 514/9 |
| 2009/0286764 A1 | | 11/2009 | Kipp et al. | |
| 2009/0291996 A1 | | 11/2009 | Korodi et al. | |
| 2009/0324635 A1 | | 12/2009 | Korodi et al. | |
| 2010/0137197 A1 | * | 6/2010 | Mittal et al. ................... | 514/9 |
| 2010/0168415 A1 | | 7/2010 | Lee et al. | |
| 2010/0256074 A1 | | 10/2010 | Eidelman et al. | |
| 2011/0014676 A1 | | 1/2011 | Cowan et al. | |
| 2013/0184433 A1 | | 7/2013 | De Pater et al. | |
| 2014/0005355 A1 | | 1/2014 | Kothakonda et al. | |
| 2014/0058082 A1 | | 2/2014 | Zhang et al. | |
| 2014/0142032 A1 | * | 5/2014 | Jiang et al. ................. | 514/3.6 |
| 2015/0072923 A1 | | 3/2015 | Shirode et al. | |
| 2016/0068564 A1 | | 3/2016 | De Pater et al. | |
| 2016/0215021 A1 | | 7/2016 | Groen et al. | |

FOREIGN PATENT DOCUMENTS

| | | | | |
|---|---|---|---|---|
| CA | 2375779 | | 12/2000 | |
| CA | CA 2375779 | * | 12/2000 | ............ A61K 38/22 |
| CN | 102166186 | | 8/2011 | |
| WO | 2008012310 | | 1/2008 | |
| WO | 2010032011 | | 3/2010 | |
| WO | 2012038371 | | 3/2013 | |

OTHER PUBLICATIONS

International Searching Authority, "International Search Report and Written Opinion for PCT/US2012/071215", May 6, 2013, Publisher: European Patent Office, Published in: EPO.

Chan, et al. , "Compatibility of Caspofungin Acetate Injection with Other Drugs During Simulated Y-Site Coadministration", "IJPC", 2008, pp. 276-278, vol. 12, No. 3.

Chu, et al, "Abstract of Progress in treatment of systemic fungal injections with drugs", "Zhongguo Yiyuan Yaoxue Zazhi", 2003, pp. 560-562.

Kartsonis, et al., "Caspofungin: the first in a new class of antifungal agents", 2003, pp. 197-218, vol. 6.

Keating, et al., "Caspofungin: A Review of its Use in Oesophageal Candidiasis, Invasive Candidiasis and Invasive Aspergillosis", "Adis Drug Evaluation", 2003, pp. 2235-2263.

Morrison, Vicki A. , "Caspofungin: an overview", "Expert Rev. Anti Infect Ther.", 2005, pp. 697-705, vol. 3, No. 5.

Nerurkar, et al., "On the Development of a Lyophilized Formulation of L-743,872", "Pharm. Res.", 1996, pp. S-226, vol. 13, No. 9.

(Continued)

*Primary Examiner* — Maury Audet
(74) *Attorney, Agent, or Firm* — Pitts & Lake, P.C.

(57) ABSTRACT

A caspofungin composition includes caspofungin acetate and at least one amino acid, where the composition is a solid. The solid composition may be made by forming a liquid mixture including a solvent, caspofungin acetate and the amino acid(s), and lyophilizing the liquid mixture.

22 Claims, 3 Drawing Sheets

(56) References Cited

OTHER PUBLICATIONS

Obach, et al., "Trend Analysis of a Database of Intravenous Pharmacokinetic Parameters in Humans for 670 Drug Compounds", "Drug Met. Disp.", 2008, pp. 1385-1405, vol. 36, No. 7.

Tsiouris, et al., "Stability and Compatibility of Reconstituted Caspofungin in Select Elastomeric Infusion Devices", "IJPC", 2010, pp. 436-439, vol. 14, No. 5.

Merck & Co, Inc. , "Cancidas: Highlights of Prescribing Information", "Product information for Cancidas", 2010, pp. 1-24.

Scientific Discussion on Caspofungin MSD; Cancidas: EPAR—Scientific Discussion, EPAR, p. 2, par. 6, Oct. 21, 2005.

Cohen, Victor et al., "Room-temperature storage of medications labeled for refrigeration", Aug. 15, 2007, pp. 1711-1715, vol. 64, Publisher: American Journal of Health System Pharmacy.

Zhang, Jeney et al., "Stabilization of vaccines and antibiotics in silk and eliminating the cold chain", Jul. 24, 2012, pp. 11981-11986, vol. 109, No. 30, Publisher: Proceedsing of the National Academy of Sciences of the United States of America.

"Scientific Discussion on Caspofungin MSD; Cancidas: EPAR—Scientific Discussion, EPAR, Entire Document, Oct. 21, 2005".

* cited by examiner

CASPOFUNGIN ACETATE FORMULATIONS

REFERENCE TO RELATED APPLICATIONS

This application claims the benefit of U.S. Provisional Application No. 61/728,406 entitled "Caspofungin Acetate Formulations" filed Nov. 20, 2012, which is incorporated by reference in its entirety.

BACKGROUND

A variety of fungal infections can occur in patients due to pathogenic *Candida* or *Aspergillus* fungus species. Examples of such fungal infections include candidemia, candidiasis (including esophageal infections, abdominal infections, pleural space infections and peritoneal infections), and invasive aspergillosis. Early antifungal agents typically attacked the inner cell membrane of the invasive fungus. These early agents had a variety of drawbacks, however, including toxic side effects, drug-drug interactions, variations in efficacy between patients, and fungal resistance.

A more recent family of antifungal agents is the echniocandins, which treat fungal infections through a different mechanism—inhibition of the enzyme that forms β-(1,3)-D-glucan, an essential component of the fungal outer cell wall. Since β-(1,3)-D-glucan does not occur naturally in the cell walls of mammals, the action of echinocandins is unlikely to be harmful to the cells of an infected patient. Due to the difference in their mechanism of action relative to earlier agents, echinocandins have not experienced wide resistance by target fungi.

Figure 1:
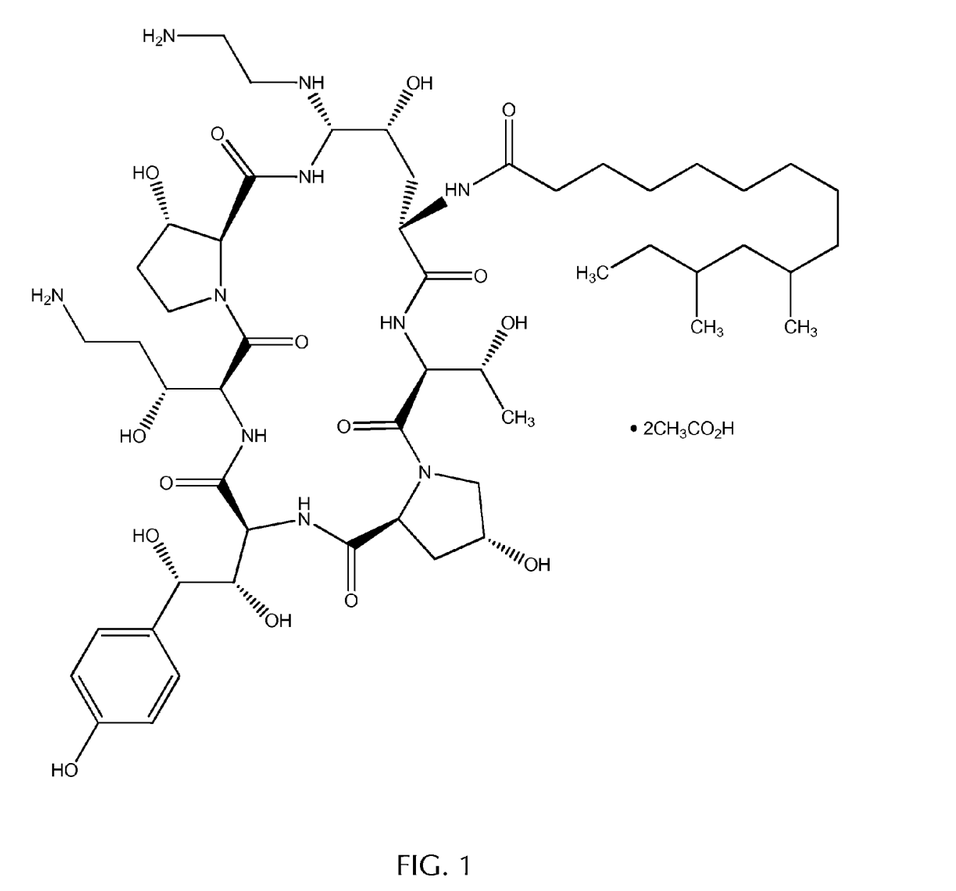
FIG. 1 depicts a chemical structure of caspofungin acetate.

Caspofungin acetate was the first of the echinocandins to be approved in the U.S. for use as an antifungal agent. The full name for caspofungin acetate is reported as 1-[(4R,5S)-5-[(2-aminoethyl)amino]-$N^2$-(10,12-dimethyl-1-oxotetradecyl)-4-hydroxy-L-ornithine]-5-[(3R)-3-hydroxy-L-ornithine]pneumocandin $B_0$ diacetate (salt), and a representative chemical structure of caspofungin acetate is shown in FIG. 1. An approved treatment regimen for adults includes an initial administration of 70 milligrams (mg) caspofungin acetate, followed by daily administration of 50 mg caspofungin acetate, where each administration is performed through intravenous infusion over 1 hour.

As caspofungin acetate has poor oral bioavailability, it typically has been provided to medical personnel as a lyophilized solid, which is then reconstituted before intravenous administration to a patient. In one example, a formulation of caspofungin acetate that is commercially available at present is sold under the CANCIDAS® trademark. CANCIDAS® for Injection (Merck & Co, Inc.; Whitehouse Station, N.J., USA) is currently available as a lyophilized powder. CANCIDAS® is available in vials containing either 54.6 mg or 75.6 mg of caspofungin acetate, in combination with sucrose and mannitol, and including acetic acid and sodium hydroxide as pH modifiers. CANCIDAS® is reconstituted for administration by combining the lyophilized powder with 10.8 milliliters (mL) of a reconstitution liquid (such as 0.9% sodium chloride), to provide a solution having a caspofungin acetate concentration of either 7 milligrams per milliliter (mg/mL) or 5 mg/mL. This reconstituted liquid typically is diluted with an infusion liquid prior to administration.

One challenge associated with the commercially available formulation of caspofungin acetate is its instability, including its instability at ambient temperatures. Degradation products of caspofungin acetate at room temperature (~25° C.) include various dimers of caspofungin, as well as other substances. Current protocols require caspofungin acetate to be stored at −70° C. (±10° C.), and require the lyophilized CANCIDAS® formulation to be stored at temperatures of 2-8° C. A reconstituted liquid formed from the CANCIDAS® formulation must be diluted within one hour, and then either administered within 24 hours or stored at 2-8° C. for up to 48 hours. These temperature and time constraints present potential difficulties for effective administration of caspofungin acetate, both in medical professional settings and in outpatient settings. See, for example, Tsiouris, Maria et al. "Stability and compatibility of reconstituted caspofungin in select elastomeric infusion devices", *International Journal of Pharmaceutical Compounding* (2010), 14(5), 436-439.

Various reformulations have been reported to improve the stability of caspofungin. The use of the acetate salt form of caspofungin was an initial effort at improving the stability of caspofungin, as earlier versions of caspofungin formulations used the tartrate salt instead. Thus, the CANCIDAS® formulation, which includes caspofungin in its acetate salt form, has improved stability relative to formulations of caspofungin tartrate. See U.S. Pat. No. 5,952,300, column 2, lines 22-56 and column 8, lines 11-67.

In another example, the pH modifiers acetic acid and sodium hydroxide were eliminated from the CANCIDAS® formulation, and the resulting formulations had improved stability at ambient temperatures. Lyophilized formulations were more stable with respect to caspofungin at 25° C. for 12 weeks, and reconstituted solutions of the formulations were more stable with respect to the caspofungin at 25° C. for 2 days. See US 2009/0170753, paragraphs [0080], [0204]-[0207] and [0214]-[0217].

In another example, the sucrose and mannitol in the CANCIDAS® formulation were replaced with a non-reducing sugar such as trehalose, and the resulting formulations had improved stability at ambient temperatures. Lyophilized formulations containing trehalose more were stable with respect to caspofungin at 30° C. for up to 72 weeks, and at 40° C. for up to 24 weeks. See US 2010/0137197, paragraphs [0114]-[0119].

It is desirable to have caspofungin acetate formulations that can be stored as lyophilized solids without the need for control of the surrounding temperature. For example, it is desirable for a lyophilized formulation of caspofungin acetate to be stable at temperatures of 25° C. or higher for a period of from 6 months to 2 years. Preferably such stabilized formulations would be convenient to prepare, store, reconstitute and administer.

SUMMARY

In one aspect, the invention provides a composition including caspofungin acetate and at least one amino acid, where the composition is a solid.

In another aspect of the invention, there is a composition including from 50 to 70 mg caspofungin acetate, and arginine. The mass ratio of arginine to caspofungin acetate is from 2:5 to 3:1, and the composition is a solid.

In another aspect of the invention, there is a composition, formed by a method including forming a liquid mixture that includes a solvent, caspofungin acetate and at least one amino acid, and lyophilizing the liquid mixture to form a solid composition.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention.

DETAILED DESCRIPTION

Lyophilized formulations that include caspofungin acetate and an amino acid can protect caspofungin acetate from degradation. These formulations may be stored at room temperature for up to two years, and thus may not require storage in a refrigerator or freezer prior to use. Reconstitution of the lyophilized formulations with a carrier liquid can yield an injectable liquid that may be used to administer caspofungin acetate.

A composition may include caspofungin acetate, at least one amino acid and optionally one or more other substances, where the composition is a solid. The solid composition may be prepared by forming a liquid mixture including a solvent, caspofungin acetate and at least one amino acid, and then lyophilizing the mixture. The resulting solid composition may be used in administering caspofungin acetate to a patient by combining the composition with an aqueous carrier to form a solution or emulsion, which, for example, can be injected into a patient.

Caspofungin acetate is a salt of one equivalent of caspofungin and two equivalents of acetic acid, providing an empirical formula of $C_{52}H_{88}N_{10}O_{15} \cdot 2C_2H_4O_2$, and a formula weight of 1,213.42 grams per mole. The chemical structure shown in FIG. 1 represents caspofungin acetate in its associated form. Caspofungin acetate may dissociate from one or both of its equivalents of acetic acid in the presence of a solvent; however, the salt still includes both the cyclic caspofungin and the acetic acid species. Thus, the term "caspofungin acetate" includes both an associated combination of caspofungin and acetic acid, as well as caspofungin and acetic acid in a dissociated state, such as may occur when the salt is combined with a solvent.

Caspofungin acetate does not include salts of caspofungin with substances other than acetic acid. For example, it has been reported that caspofungin can form pharmaceutically acceptable salts with substances including cations such as sodium, potassium, aluminum, calcium, lithium, magnesium and zinc; acids such as hydrochloric, hydrobromic, phosphoric, sulfuric, maleic, citric, tartaric, succinic, oxalic, malic, glutamic, lactic, propionic and pamoic acids; and bases such as ammonia, ethylenediamine, N-methyl-glutamine, lysine, arginine, ornithine, choline, N,N'-dibenzylethylene-diamine, chloroprocaine, diethanolamine, procaine, N-benzylphenethylamine, diethylamine, piperazine, tris(hydroxymethyl)aminomethane and tetramethyl-ammonium hydroxide. See U.S. Pat. No. 5,378,804 at column 1, line 67-column 2, line 5; U.S. Pat. No. 5,936,062 at column 2, lines 47-67; and US 2009/0170753 at paragraphs 35-36. These alternative salts, however, do not include acetic acid species, and thus are not included in the term "caspofungin acetate".

A solid composition that includes caspofungin acetate and an amino acid may include an amount of caspofungin acetate that is sufficient for a single initial dose of caspofungin acetate, or an amount sufficient for a daily maintenance dose of caspofungin acetate. A solid composition that includes caspofungin acetate and an amino acid may include an amount of caspofungin acetate that is sufficient for two or more initial doses of caspofungin acetate, or an amount sufficient for two or more daily maintenance doses of caspofungin acetate. The amount of caspofungin acetate in the composition may be a different therapeutic amount. For example, the amount of caspofungin acetate in the composition may be an amount sufficient for half of a single initial dose, or for half of a daily maintenance dose.

In one example, a solid composition that includes caspofungin acetate and an amino acid may include from 10 to 150 milligrams (mg) caspofungin acetate. Preferably the composition includes from 25 to 100 mg caspofungin acetate, or from 50 to 70 mg caspofungin acetate. Presently preferred amounts of caspofungin acetate in the composition include about 50 mg and about 70 mg.

Figure 2A:
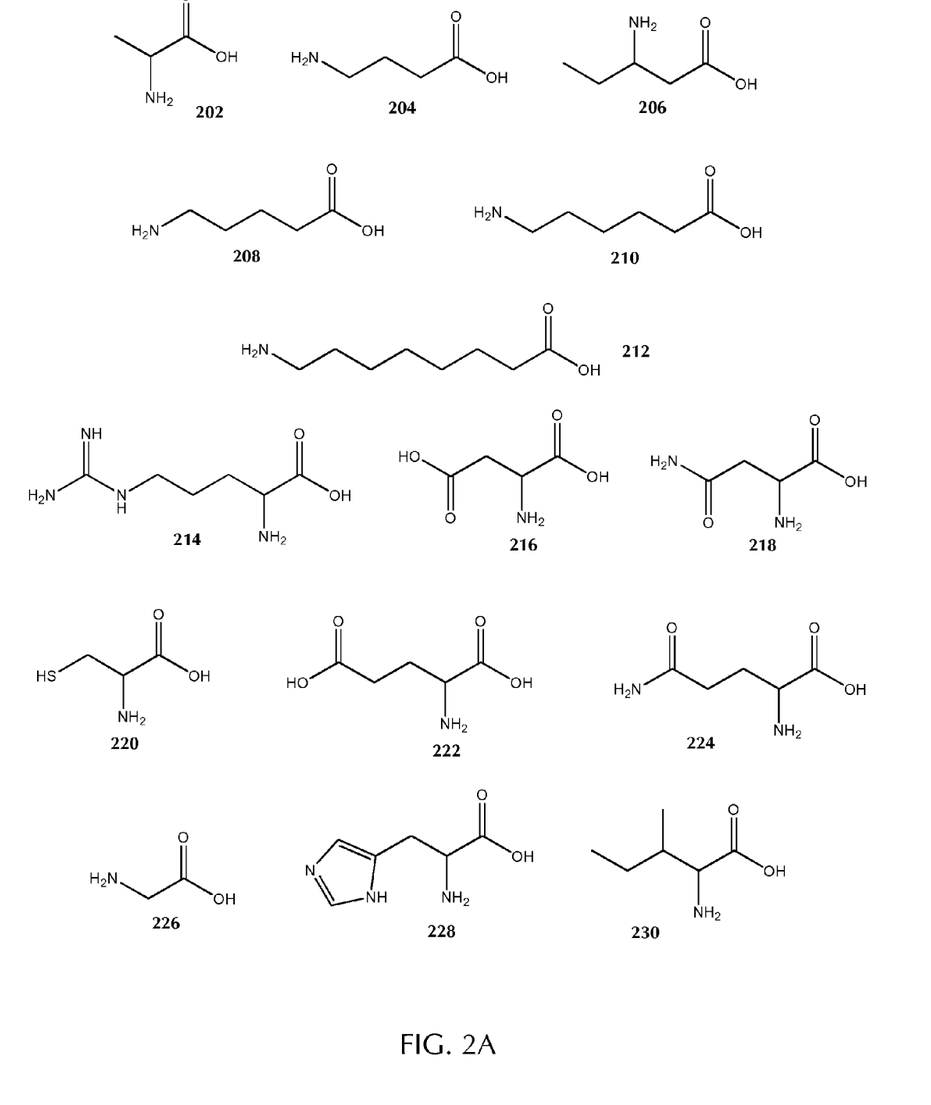
FIGS. 2A and 2B depict chemical structures of examples of amino acids.
Figure 2B:
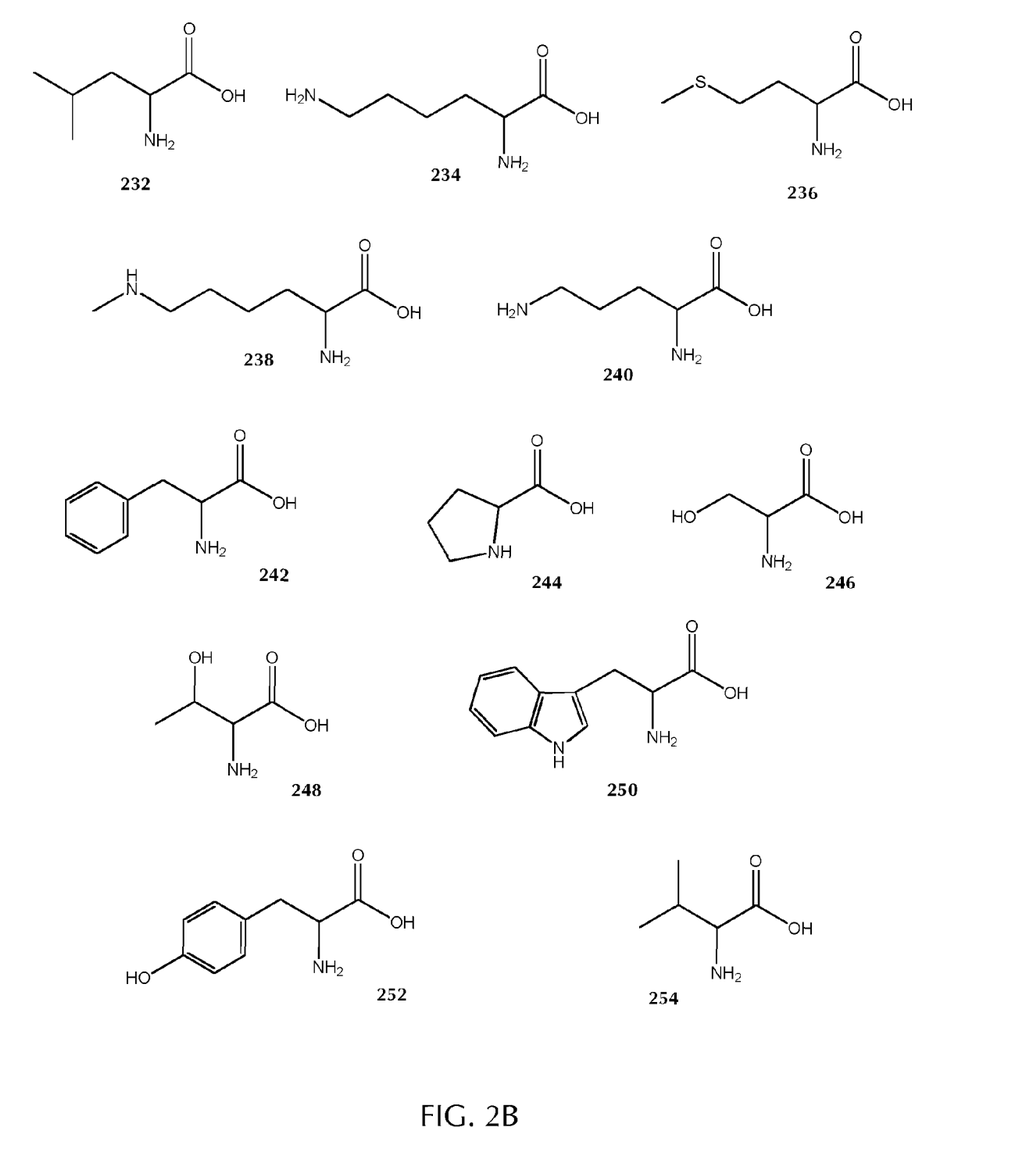

A solid composition that includes caspofungin acetate and an amino acid includes one or more amino acids, which are compounds containing at least one carboxylic acid group [—C(═O)OH] and at least one primary or secondary amine group [—$NH_2$ or —RNH, where —R is a molecular entity other than —H], but lacking a secondary amide group [—C(═O)—NH—]. FIG. 2 depicts chemical structures of examples of amino acids, including alanine 202, 4-aminobutanoic acid 204, 3-aminopentanoic acid 206, 5-aminopentanoic acid 208, 6-aminohexanoic acid 210, 8-aminooctanoic acid 212, arginine 214, aspartic acid 216, asparagine 218, cysteine 220, glutamic acid 222, glutamine 224, glycine 226, histidine 228, isoleucine 230, leucine 232, lysine 234, methionine 236, methyl lysine 238, ornithine 240, phenylalanine 242, proline 244, serine 246, threonine 248, tryptophan 250, tyrosine 252 and valine 254. Other amino acids, including isomers and substituted derivatives of the amino acids depicted in FIG. 2, may be present in the composition.

Presently preferred amino acids for use in the solid compositions that include caspofungin acetate and at least one amino acid include 6-aminohexanoic acid 210, arginine 214, asparagine 218, glycine 226, lysine 234, methyl lysine 238, and ornithine 240. A solid composition that includes caspofungin acetate and an amino acid may include one or more amino acids that contain at least two primary or secondary amine groups. Examples of amino acids containing at least two primary or secondary amine groups include arginine 214, asparagine 218, lysine 234, methyl lysine 238, and ornithine 240.

Surprisingly, it has been discovered that a solid composition including caspofungin acetate and an amino acid may be more stable than a solid composition including caspofungin acetate, mannitol and sucrose, such as the CANCIDAS® formulation (Merck & Co, Inc.). It is presently believed that solid compositions that include caspofungin acetate and an amino acid may be able to protect caspofungin acetate from degradation for a year or longer at room temperature (~25° C.), and for 6 months or longer at elevated temperatures.

The amino acids arginine, asparagine and glycine can stabilize caspofungin acetate in solid compositions. Table 1 lists the results of stability analyses of lyophilized compositions of caspofungin acetate with arginine 214, asparagine 218 and glycine 226, and for a conventional lyophilized composition of caspofungin acetate with mannitol and sucrose. For each solid composition listed in Table 1 that included an amino acid, 50 mg caspofungin acetate was combined with the listed amino acid and with water for injection (USP), and the pH was adjusted to about 6.0. The aqueous mixtures were then lyophilized to provide solid powders. Samples of each solid composition were sealed in vials at temperatures of 5° C., 25° C. or 40° C. The stability of the caspofungin acetate in the compositions over time at each temperature was determined by analyzing samples by High Pressure Liquid Chromatography (HPLC) and then calculating the total amount of relevant impurities of caspofungin detected in each HPLC analysis by peak area percent. The HPLC analysis was performed using a reversed phase HPLC having a variable wavelength UV/VIS detector and a C-18 column (2.7 micron, 150×4.6 mm ID). The liquid sample was passed through the HPLC using gradient elution at a flow rate of 1.0 mL/min and a temperature of 25° C. The impurities were detected using UV-detection at 225 nm, where the limit of quantification was <0.05%. Table 1 lists the percent total impurities measured for the lyophilized compositions.

TABLE 1

Stability of Caspofungin Acetate Compositions

| | | Excipient: | | | | |
|---|---|---|---|---|---|---|
| | | Glycine | Arginine | Asparagine | | Mannitol + Sucrose* |
| | | | Mass Ratio Amino Acid:Caspofungin Acetate: | | | |
| | | 1:1 | 1:1 | 2:1 | 2:5 | 3:5 | — |
| Time (days) | Temperature (° C.) | Moisture content (%): | | | | |
| | | 0.50 | 0.54 | 1.24 | 0.87 | 1.45 | — |
| | | Total Impurities (%) | | | | |
| 4 | 5 | 1.61 | 0.60 | — | — | 1.05 | — |
| 7 | | 1.57 | 0.65 | 0.62 | 0.80 | 1.05 | — |
| 14 | | 1.62 | 0.67 | 0.58 | 1.02 | 1.09 | — |
| 29 | | 1.98 | — | 0.61 | 1.28 | 1.48 | — |
| 7 | 25 | 4.78 | 0.69 | 0.65 | 1.85 | 2.64 | 2.06 |
| 14 | | 6.19 | 0.67 | 0.62 | 1.87 | 4.48 | — |
| 29 | | 7.44 | 0.73 | 0.65 | 3.41 | 4.75 | 2.09 |
| 7 | 40 | 13.77 | 1.10 | 0.76 | 5.77 | 7.36 | 6.34 |
| 14 | | 17.98 | 1.32 | 0.82 | 7.87 | 11.91 | — |
| 29 | | 21.30 | 1.62 | 0.91 | 13.66 | 13.14 | 23.65 |
| 56 | | — | 2.23 | 1.37 | — | — | — |

*Conventional formulation; 1.93% total impurities at time = 0 days

The solid composition having a mass ratio of arginine 214 to caspofungin acetate of 2:1 had the lowest level of impurities of the compositions listed in Table 1, from the initial days of the analysis and up to 56 days at 40° C. When stored at 5° C., 25° C. (~room temperature), and 40° C. for 29 days, the impurity levels for this composition were only 0.61%, 0.65% and 0.91% respectively.

This 2:1 arginine composition was more stable than the conventional mannitol and sucrose composition at each time and temperature for which comparative results are listed. When stored at 25° C. for 7 days, the level of impurities in the solid composition having a mass ratio of arginine to caspofungin acetate of 2:1 was 68% less than the level of impurities in the conventional mannitol and sucrose composition [68%=100%×(2.06%−0.65%)/2.06%]. When stored at 25° C. for 29 days, the level of impurities in the solid composition having a mass ratio of arginine to caspofungin acetate of 2:1 was 69% less than the level of impurities in the conventional mannitol and sucrose composition [69%=100%×(2.09%−0.65%)/2.09%]. When stored at 40° C. for 7 days, the level of impurities in the solid composition having a mass ratio of arginine to caspofungin acetate of 2:1 was 88% less than the level of impurities in the conventional mannitol and sucrose composition [88%=100%×(6.34%−0.76%)/6.34%]. When stored at 40° C. for 29 days, the level of impurities in the solid composition having a mass ratio of arginine to caspofungin acetate of 2:1 was 96% less than the level of impurities in the conventional mannitol and sucrose composition [96%=100%×(23.65%−0.91%)/23.65%].

When subjected to extended storage for 8 weeks (56 days) at an elevated temperature of 40° C., this 2:1 arginine composition maintained a total impurity level of 1.37%, which is acceptable under the International Conference on Harmonization of Technical Requirements for Registration of Pharmaceuticals for Human Use (ICH). Based on this acceptable stability under these accelerated aging conditions, it is presently believed that a solid composition including caspofungin acetate and arginine in a 2:1 mass ratio of amino acid to caspofungin acetate will be stable for up to 2 years at room temperature, and will be stable for 6 months or longer at 40° C.

The effect of arginine 214 on the stability of caspofungin acetate in a solid composition appeared to be related to the relative amount of amino acid in the composition. The solid composition having a mass ratio of arginine to caspofungin acetate of 1:1 had a higher level of impurities than did the solid composition having a mass ratio of arginine to caspofungin acetate of 2:1, at each time and temperature for which comparative results are listed.

Despite this decrease in stability, the composition having the lower mass ratio of arginine to caspofungin acetate of 1:1 was still more stable than the conventional mannitol and sucrose composition at each temperature for which comparative results are listed. When stored at 25° C. for 7 days, the level of impurities in the solid composition having a mass ratio of arginine to caspofungin acetate of 1:1 was 67% less than the level of impurities in the conventional mannitol and sucrose composition [67%=100%×(2.06%−0.69%)/2.06%]. When stored at 25° C. for 29 days, the level of impurities in the solid composition having a mass ratio of arginine to caspofungin acetate of 1:1 was 65% less than the level of impurities in the conventional mannitol and sucrose composition [65%=100%×(2.09%−0.73%)/2.09%]. When stored at 40° C. for 7 days, the level of impurities in the solid composition having a mass ratio of arginine to caspofungin acetate of 1:1 was 83% less than the level of impurities in the conventional mannitol and sucrose composition [83%=100%×(6.34%−1.10%)/6.34%]. When stored at 40° C. for 29 days, the level of impurities in the solid composition having a mass ratio of arginine to caspofungin acetate of 1:1 was 93% less than the level of impurities in the conventional mannitol and sucrose composition [93%=100%×(23.65%−1.62%)/23.65%].

The stabilizing effect of asparagine 218 with regard to caspofungin acetate in a solid composition was less than the stabilizing effect of arginine. The solid compositions having mass ratios of asparagine to caspofungin acetate of 2:5 or 3:5 had higher levels of impurities than did the solid compositions having a mass ratio of arginine to caspofungin acetate of 2:1 or 1:1, at each time and temperature for which comparative results are listed. Compositions having a mass ratio of arginine to caspofungin acetate greater than 3:5 were not analyzed due to the lower aqueous solubility of asparagine in comparison to arginine. Despite this decrease in stability relative to compositions containing arginine, the stability of caspofungin acetate in compositions containing asparagine was comparable to that of the conventional mannitol and sucrose composition. Moreover, when stored at 40° C. for 29 days, the level of impurities in the solid compositions having mass ratios of asparagine to caspofungin acetate of 2:5 or 3:5 were 42-44% less than the level of impurities in the conventional mannitol and sucrose composition [(42%=100%×(23.65%−13.66%)/23.65%); (44%=100%×(23.65%−13.14%)/23.65%)].

The stabilizing effect of glycine 226 with regard to caspofungin acetate in a solid composition was less than the stabilizing effects of either arginine or asparagine. The solid composition having a mass ratio of glycine to caspofungin acetate of 1:1 had higher levels of impurities than did the solid compositions containing arginine or asparagine, at each time and temperature for which comparative results are listed. As noted in Tables 2 and 4 below, the mass ratio of glycine to caspofungin acetate could be higher than 1:1, such as 2:1 or 3:1.

Despite this decrease in stability relative to compositions containing arginine, the compositions of caspofungin acetate with glycine were still more stable overall than the conventional mannitol and sucrose composition when stored for 29 days at 40° C. When stored at 40° C. for 29 days, the level of impurities in the solid composition having a mass ratio of glycine to caspofungin acetate of 1:1 was 10% less than the level of impurities in the conventional mannitol and sucrose composition [10%=100%×(23.65%−21.30%)/23.65%].

A variety of amino acids other than arginine, asparagine and glycine also can stabilize caspofungin acetate in solid compositions. Table 2 lists the results of stability analyses of lyophilized compositions of caspofungin acetate with the amino acids 6-aminohexanoic acid 210, arginine 214, glycine 226, lysine 234, methyl lysine 238 and ornithine 240. For each solid composition listed in Table 2, 50 mg caspofungin acetate was combined with the listed amino acid and with water for injection (USP), and the pH was adjusted. The aqueous mixtures were then lyophilized to provide solid powders. Samples of each solid composition were sealed in vials at temperatures of 25° C., 40° C. or 55° C. The stability of the caspofungin acetate in the compositions over time at each temperature was determined by analyzing samples by HPLC and then calculating the total amount of relevant impurities detected in each HPLC analysis by peak area percent, as described above with regard to the results of Table 1. Table 2 lists the percent total impurities measured for the lyophilized compositions.

Of the solid compositions listed in Table 2, the composition having a mass ratio of arginine 214 to caspofungin acetate of 1:1 had the lowest level of impurities at elevated temperatures of 40° C. and 55° C., maintaining total impurity levels below 5% for the times and temperatures listed. The compositions containing 6-aminohexanoic acid 210, lysine 234, methyl lysine 238 or ornithine 240 were less stable than the arginine composition, having total impurity levels of 5.87%-13.80% at an elevated temperature of 40° C. for 4 weeks, and total impurity levels of 16.65%-33.38% at an elevated temperature of 55° C. for 2 weeks. The composition containing glycine 226 was the least stable of the amino acid compositions, having a total impurity level of 28.88% at an elevated temperature of 40° C. for 4 weeks, and a total impurity level of 44.70% at an elevated temperature of 55° C. for 2 weeks.

Arginine can be used in different amounts relative to the amount of caspofungin acetate in solid compositions. Table 3 lists the results of stability analyses of lyophilized compositions of caspofungin acetate having mass ratios of arginine 214 to caspofungin acetate of 1:1 or 2:1. For each solid composition listed in Table 3, 50 mg caspofungin acetate was combined with the listed amino acid and with water for injection (USP), and the pH was adjusted. The aqueous mixtures were then lyophilized to provide solid powders. Samples of each solid composition were sealed in vials at temperatures of 25° C., 40° C. or 55° C. The stability of the caspofungin acetate in the compositions over time at each temperature was determined by analyzing samples by HPLC and then calculating the total amount of relevant impurities detected in each HPLC analysis by peak area percent, as described above with regard to the results of Table 1. Table 3 lists the percent total impurities measured for the lyophilized compositions.

TABLE 2

Caspofungin Acetate (CA) Compositions Containing Amino Acids (AA)

| | | Amino acid (AA): | | | | | |
|---|---|---|---|---|---|---|---|
| | | Arginine | Glycine | Ornithine | Lysine | 6-amino-hexanoic acid | methyl lysine |
| | | Mass Ratio (AA:CA): | | | | | |
| | | 1:1 | 3:1 | 2:1 | 2:1 | 2:1 | 2:1 |
| | | pH*: | | | | | |
| | | 6.55 | 7.21 | 6.46 | 6.66 | 6.65 | 6.36 |
| | | Moisture content (%): | | | | | |
| Time (weeks) | Temperature (° C.) | 0.67 | 1.36 | 0.56 | 0.64 | 0.64 | 0.46 |
| | | Total Impurities (%) | | | | | |
| 0 | — | 0.78 | 1.53 | 1.14 | 0.84 | 0.86 | 0.68 |
| 2 | 25 | — | 9.70 | 5.01 | 2.72 | 2.66 | 0.92 |
| 4 | | — | 10.55 | 4.01 | 3.13 | 3.97 | 0.94 |
| 8 | | — | — | — | — | — | 1.28 |
| 2 | 40 | 1.53 | 20.15 | 8.14 | 6.07 | 9.13 | 4.18 |
| 4 | | 2.23 | 28.88 | 12.80 | 8.09 | 13.80 | 5.87 |
| 8 | | 2.61 | — | — | — | — | — |
| 12 | | 2.56 | — | — | — | — | — |
| 2 | 55 | 2.87 | 44.70 | 18.51 | 16.65 | 29.82 | 33.38 |
| 4 | | 4.42 | — | — | — | — | — |

*pH of liquid when reconstituted in water for injection.

TABLE 3

Caspofungin Acetate (CA) Compositions Containing Amino Acids (AA)

| | | Amino acid (AA): Arginine | | | |
|---|---|---|---|---|---|
| | | Mass Ratio (AA:CA): | | | |
| | | 1:1 | 2:1 | 2:1 | 2:1 |
| | | pH*: | | | |
| | | 6.55 | 5.77 | 6.74 | 7.46 |
| | | Moisture content (%): | | | |
| Time (weeks) | Temperature (° C.) | 0.67 | — | — | — |
| | | Total Impurities (%) | | | |
| 0 | — | 0.78 | 1.25 | 1.28 | 1.50 |
| 12 | 25 | — | 1.53 | 1.63 | 1.68 |
| 2 | 40 | 1.53 | — | — | — |
| 4 | | 2.23 | 1.91 | 2.03 | 2.12 |
| 8 | | 2.61 | 2.73 | 2.42 | 2.52 |
| 12 | | 2.56 | 2.84 | 2.69 | 2.77 |
| 2 | 55 | 2.87 | 3.82 | 3.96 | 4.08 |
| 4 | | 4.42 | 4.81 | 4.91 | 5.39 |

*pH of liquid when reconstituted in water for injection.

The solid compositions having mass ratios of arginine 214 to caspofungin acetate of 1:1 or 2:1 listed in Table 3 had good stability of the caspofungin acetate. When stored at 40° C. for up to 12 weeks, each of the listed compositions maintained total impurity levels below 3%. When stored at 55° C., the composition having an alkaline pH upon reconstitution had slightly less stability of the caspofungin acetate than did the compositions having acidic pH's. Each of the listed compositions, however, maintained total impurity levels below 5.5% when stored at 55° C. for up to 4 weeks.

The stabilization of caspofungin acetate by amino acids is surprising and unexpected, as shown by comparing the stabilities of solid compositions of caspofungin acetate in combination with a typical lyophilization stabilizing agent and/or glycine. Solid compositions of caspofungin acetate containing hydroxyethyl starch (HES) were less stable than were solid compositions of caspofungin acetate containing glycine. As HES is a typical lyophilization stabilizing agent, the improvement in caspofungin acetate stabilization that occurs when HES is replaced with glycine is not due to a simple replacement of one known stabilizing agent with another stabilizing agent. Moreover, since glycine was the least effective stabilizer of the amino acids listed in Tables 1 and 2 above, the improvement in stabilization achieved by replacing the HES with an amino acid is not a result of optimization of the amino acid composition.

Table 4 lists the results of stability analyses of lyophilized compositions of caspofungin acetate with HES and/or glycine. For each formulation listed in Table 4, 50 mg caspofungin acetate was combined with the listed excipient(s) and with water for injection (USP), and the pH was adjusted to about 6.0. The aqueous mixtures were then lyophilized to provide solid powders. Samples of each formulation were sealed in vials at temperatures of 5° C., 25° C. or 40° C. The stability of the caspofungin acetate in the formulations over time at each temperature was determined by analyzing samples by HPLC and then calculating the total amount of relevant impurities detected in each HPLC analysis by peak area percent, as described above with regard to the results of Table 1. Table 4 lists the percent total impurities for lyophilized formulations of caspofungin acetate with the excipients HES and/or glycine.

TABLE 4

Stability of Caspofungin Acetate Compositions Containing HES and/or Glycine

| | | Excipient: | | | | |
|---|---|---|---|---|---|---|
| | | | | HES + Glycine (1:1) | | Glycine |
| | | HES | | | | |
| | | Mass Ratio (Excipient:Caspofungin Acetate): | | | | |
| | | 2:1 | 2:1 | 2:1 | 1:1 | 1:1 |
| | | Moisture content (%): | | | | |
| Time (days) | Temperature (° C.) | 0.62 | 0.39 | 0.49 | 0.53 | 1.29 |
| | | Total Impurities (%) | | | | |
| 0 | — | 2.10 | 1.25 | 0.81 | 0.90 | 1.02 |
| 7 | 5 | 2.90 | 1.57 | 0.90 | 1.08 | 1.12 |
| 14 | | 2.85 | 1.61 | 0.85 | 1.09 | — |
| 28 | | 3.40 | 1.75 | 0.84 | 1.09 | 1.31 |
| 7 | 25 | 6.48 | 3.39 | 1.48 | 2.09 | 2.58 |
| 14 | | 8.79 | 4.30 | 1.90 | 2.67 | 3.59 |
| 28 | | 10.15 | 5.89 | 2.68 | 3.76 | 5.31 |
| 7 | 40 | 18.04 | 12.21 | 5.10 | 7.87 | 8.08 |
| 14 | | 24.71 | 16.98 | 7.59 | 12.52 | 13.17 |
| 28 | | — | — | 9.40 | 13.76 | — |

The HES formulation (mass ratio of HES to caspofungin acetate of 2:1) had a high level of impurities even at the beginning of the analysis. The 2.10% impurity level at the beginning of the analysis rose to 3.40%, 10.15% and 24.71% after storage for 28 days at 5° C., for 28 days at 25° C. (~room temperature), and for 14 days at 40° C., respectively.

Substituting half of the HES excipient with glycine reduced the amount of impurities in the formulation relative to the amounts in the 2:1 HES formulation. Substituting half of the HES excipient with glycine reduced the amount of impurities at the beginning of the analysis by 41% [40.5%=100%×(2.10%−1.25%)/2.10%], reduced the amount of impurities after storage for 28 days at 5° C. by 49% [48.5%=100%×(3.40%−1.75%)/3.40%], reduced the amount of impurities after storage for 28 days at 25° C. by 42% [42.0%=100%×(10.15%−5.89%)/10.15%], and reduced the amount of impurities after storage for 14 days at 40° C. by 31% [31.3%=100%×(24.71%−16.98%)/24.71%].

Substituting the remaining HES excipient with glycine further reduced the amount of impurities in the formulation. The formulations with glycine but without HES as an excipient (mass ratio of glycine to caspofungin acetate of 1:1 or 2:1), had impurity levels of approximately 1% or lower at the beginning of the analysis. Substituting the remaining HES excipient with glycine (mass ratio glycine to caspofungin acetate of 2:1) further reduced the amount of impurities at the beginning of the analysis by 35% [35.2%=100%×(1.25%−0.81%)/1.25%], further reduced the amount of impurities after storage for 28 days at 5° C. by 52% [52.0%=100%×(1.75%−0.84%)/1.75%], further reduced the amount of impurities after storage for 28 days at 25° C. by 55% [54.5%=100%×(5.89%−2.68%)/5.89%], and further reduced the amount of impurities after storage for 14 days at 40° C. by 55% [55.3%=100%×(16.98%−7.59%)/16.98%]. Overall, substituting the entire HES excipient with glycine reduced the amount of impurities at the beginning of the analysis by 61% [61.4%=100%×(2.10%−0.81%)/2.10%], reduced the amount of impurities after storage for 28 days at 5° C. by 75% [75.3%=100%×(3.40%−0.84%)/3.40%], reduced the amount of impurities after storage for 28 days at 25° C. by 74% [73.6%=100%×(10.15%−2.68%)/

10.15%], and reduced the amount of impurities after storage for 14 days at 40° C. by 69% [69.3%=100%×(24.71%−7.59%)/24.71%].

The stabilization of caspofungin acetate due to removal of HES was observed even when the concentration of the amino acid was lower than the concentration of the HES. The formulation having a mass ratio glycine to caspofungin acetate of 1:1 and a moisture content of 0.53% corresponded to removing the HES excipient from the formulation having a mass ratio of HES to glycine to caspofungin acetate of 1:1:1. Thus, removal of the HES reduced the amount of impurities at the beginning of the analysis by 28% [28.0%=100%×(1.25%−0.90%)/1.25%], reduced the amount of impurities after storage for 28 days at 5° C. by 38% [37.7%=100%×(1.75%−1.09%)/1.75%], reduced the amount of impurities after storage for 28 days at 25° C. by 36% [36.2%=100%×(5.89%−3.76%)/5.89%], and reduced the amount of impurities after storage for 14 days at 40° C. by 26% [26.3%=100%×(16.98%−12.52%)/16.98%].

Overall, switching the formulation from a mass ratio of HES to caspofungin acetate of 2:1 to a mass ratio of glycine to caspofungin acetate of 1:1 (moisture content of 0.53%) reduced the amount of impurities at the beginning of the analysis by 57% [57.1%=100%×(2.10%−0.90%)/2.10%], reduced the amount of impurities after storage for 28 days at 5° C. by 68% [67.9%=100%×(3.40%−1.09%)/3.40%], reduced the amount of impurities after storage for 28 days at 25° C. by 63% [63.0%=100%×(10.15%−3.76%)/10.15%], and reduced the amount of impurities after storage for 14 days at 40° C. by 49% [49.3%=100%×(24.71%−12.52%)/24.71%]. Thus, although the caspofungin acetate was less stable in a formulation having a glycine to caspofungin acetate mass ratio of 1:1 than in a formulation having a glycine to caspofungin acetate mass ratio of 2:1, the caspofungin acetate was still more stable when combined with glycine as the only excipient than when HES was the only excipient.

The stabilization of lyophilized caspofungin acetate in combination with an amino acid may be affected by the water content of the lyophilized solid. Referring to Table 3, an approximately 2-fold increase in water content (from 0.53% to 1.29%) of the lyophilized formulation containing a 1:1 mass ratio of glycine to caspofungin acetate resulted in a decrease in caspofungin acetate stability. Even this decreased stability, however, was an improvement over the formulations that included HES as an excipient but that had a lower moisture content. Thus, even when combined with a moisture increase of 231% [230.8%=100%×(1.29%−0.39%)/0.39%], removing the HES excipient from the formulation having a mass ratio of HES to glycine to caspofungin acetate of 1:1:1 reduced the amount of impurities at the beginning of the analysis by 18% [18.4%=100%×(1.25%−1.02%)/1.25%], reduced the amount of impurities after storage for 28 days at 5° C. by 25% [25.1%=100%×(1.75%−1.31%)/1.75%], reduced the amount of impurities after storage for 28 days at 25° C. by 10% [9.8%=100%×(5.89%−5.31%)/5.89%], and reduced the amount of impurities after storage for 14 days at 40° C. by 22% [22.4%=100%×(16.98%−13.17%)/16.98%]. Overall, switching the formulation from a mass ratio of HES to caspofungin acetate of 2:1 to a mass ratio of glycine to caspofungin acetate of 1:1, even when combined with a moisture increase of 108% [108.1%=100%×(1.29%−0.62%)/0.62%], reduced the amount of impurities at the beginning of the analysis by 51% [51.4%=100%×(2.10%−1.02%)/2.10%], reduced the amount of impurities after storage for 28 days at 5° C. by 62% [61.5%=100%×(3.40%−1.31%)/3.40%], reduced the amount of impurities after storage for 28 days at 25° C. by 48% [47.7%=100%×(10.15%−5.31%)/10.15%], and reduced the amount of impurities after storage for 14 days at 40° C. by 47% [46.7%=100%×(24.71%−13.17%)/24.71%].

The surprising and unexpected stabilization of caspofungin by amino acids may be used to prepare solid compositions including caspofungin acetate that are more stable than a conventional solid composition including caspofungin acetate, mannitol and sucrose. The surprising and unexpected stabilization of caspofungin by amino acids may be used to prepare solid compositions including caspofungin acetate that are able to protect caspofungin acetate from degradation for a year or longer at room temperature (~25° C.), and for 6 months or longer at elevated temperatures.

A solid composition that includes caspofungin acetate and an amino acid may include an amount of the amino acid sufficient to stabilize the caspofungin acetate. Preferably the amount of the amino acid in the composition is at most an amount that will dissolve in a sample of aqueous liquid, such as a volume of aqueous liquid used for reconstitution of the solid composition.

In one example, a solid composition that includes caspofungin acetate and an amino acid may include from 20 to 350 mg of the amino acid. For a solid composition that includes approximately 50 mg caspofungin acetate, the amount of amino acid in the composition preferably is from 20 to 250 mg, from 20 to 150 mg, from 20 to 100 mg, from 30 to 250 mg, from 30 to 150 mg, or from 30 to 100 mg. For a solid composition that includes approximately 70 mg caspofungin acetate, the amount of amino acid in the composition preferably is from 28 to 350 mg, from 28 to 210 mg, from 28 to 140 mg, from 42 to 350 mg, from 42 to 210 mg, or from 42 to 140 mg.

A solid composition that includes caspofungin acetate and an amino acid may have a mass ratio of amino acid to caspofungin of at least 2:5, where the mass of amino acid in the ratio accounts for all amino acid species present in the solid composition. Preferably the mass ratio of amino acid to caspofungin acetate is at least 3:5, at least 1:1 or at least 2:1. Preferably the mass ratio of amino acid to caspofungin acetate is at most 3:1 or at most 2:1. Preferably the mass ratio of amino acid to caspofungin acetate is from 2:5 to 3:1, from 3:5 to 2:1, or from 1:1 to 3:1.

A solid composition that includes caspofungin acetate and an amino acid may further include an acid and/or a base. The pH of a saturated solution of caspofungin acetate in water is about 6.6 (CANCIDAS® prescribing information, Merck Sharp & Dohme Corp., June, 2010, p. 14). The amount of the acid and/or base may be an amount sufficient to provide a pH in the range of 5 to 7 or of 6 to 7 when the composition is reconstituted in 10.8 mL of an aqueous liquid. Preferably the amount of the acid and/or base may be an amount sufficient to provide a pH in the range of 5 to 7 or of 6 to 7 when the composition is reconstituted in 10.8 mL of 0.9% aqueous sodium chloride (USP), sterile water for injection, or bacteriostatic water for injection containing either 0.9% benzyl alcohol or a combination of methylparaben and propylparaben. Presently preferred acids include hydrochloric acid. Presently preferred bases include sodium hydroxide.

A solid composition that includes caspofungin acetate and an amino acid may further include one or more other substances. Non-limiting examples of other substances include bulking agents, carriers, diluents, fillers, salts, buffers, stabilizers, solubilizers, preservatives, antioxidants, and tonicity contributors. Substances that may be useful in formulating pharmaceutically acceptable compositions, and methods of forming such compositions, are described for example in Remington: The Science and Practice of Pharmacy, 20th Ed., ed. A. Gennaro, Lippincott Williams & Wilkins, 2000, and in Kibbe, "Handbook of Pharmaceutical Excipients," 3$^{rd}$ Edition, 2000. Preferably the solid composition does not include dextrose, as caspofungin acetate is reportedly unstable when reconstituted in a liquid containing dextrose. See CANCIDAS® prescribing information, Merck Sharp & Dohme Corp., June, 2010, p. 3.

A solid composition including caspofungin acetate, at least one amino acid and optionally one or more other substances may be prepared by forming a liquid mixture that includes a solvent, caspofungin acetate, amino acid(s) and optionally one or more other substances, and lyophilizing the liquid mixture. The lyophilizing may include freeze-drying the liquid mixture to provide a solid composition. The liquid mixture may include caspofungin acetate and an amino acid in the amounts described above. The liquid mixture may further include an acid, a base and/or one or more other substances, as described above.

The liquid mixture may include from 0.1 to 5 mL solvent, from 10 to 150 mg caspofungin acetate, and from 20 to 350 mg amino acid. The liquid mixture may include from 0.5 to 2 mL solvent, from 25 to 100 mg caspofungin acetate, and from 20 to 350 mg amino acid. The liquid mixture may include from 0.75 to 1.5 mL solvent, from 50 to 70 mg caspofungin acetate, and from 20 to 350 mg amino acid. The mass ratio of amino acid to caspofungin acetate in the liquid mixture may be from 2:5 to 3:1, from 3:5 to 2:1, or from 1:1 to 3:1.

The solvent, caspofungin acetate, amino acid, optional acid, optional base and one or more other optional substances may be combined in any order when forming the liquid mixture. For example, a liquid mixture may be formed by adding the caspofungin acetate and the amino acid(s) to a container including the solvent, and then adding the acid and/or base to achieve the desired pH in the liquid mixture. The liquid mixture preferably has a pH of from 6 to 7. A presently preferred pH of the liquid mixture is 6±1.

The liquid mixture including the solvent, caspofungin acetate, amino acid, and any other optional ingredients may be lyophilized to form a solid composition, such as by subjecting the liquid mixture to freeze-drying. Freeze-drying of the liquid mixture may include maintaining the liquid mixture in an inert atmosphere, such as nitrogen or argon. Preferably the liquid mixture is placed in glass vials prior to lyophilization, and the amount of the liquid mixture in each vial is based on the amount of caspofungin acetate intended to be present in the final solid composition in the vial.

In a typical lyophilization process, the temperature of the liquid mixture is lowered to a temperature at or below the solidification point of the liquid mixture. If the liquid mixture forms a glass when cooled, the solidification point is the glass transition temperature. If the liquid mixture forms crystals when cooled, the solidification point is the eutectic point. The solidified mixture is then dried under vacuum. Typically, the drying process includes a primary drying step in which the temperature of the solidified mixture is raised gradually while most of the water is removed from the mixture by the vacuum, and a secondary drying step in which the temperature of the solidified mixture is raised further while residual moisture is removed from the mixture by the vacuum. The temperature is kept at or below the desired storage temperature for the final solid composition. Lyophilization typically is complete within 48 hours, but may require additional time. The solid composition resulting from the lyophilization typically is sealed for later use. Details regarding the lyophilization process may be found, for example, in Remington: The Science and Practice of Pharmacy, 20th Ed., ed. A. Gennaro, Lippincott Williams & Wilkins, 2000.

The lyophilized solid composition may be stored for later reconstitution and administration. Preferably the solid composition is stored at a temperature of from 10° C. to 40° C., from 15° C. to 35° C., from 20° C. to 30° C., or about 25° C. Preferably the solid composition is sealed in a glass vial to protect the composition from moisture in the surrounding environment.

A solid composition including caspofungin acetate, at least one amino acid and optionally one or more other substances may be administered to a patient by combining the composition with an aqueous carrier liquid to form an aqueous mixture, and administering the aqueous mixture into the patient by, for example, injection. Preferably, the aqueous carrier liquid is a pharmaceutically acceptable carrier liquid. Non-limiting examples of pharmaceutically acceptable carrier liquids include water and saline, such as sodium chloride injection, phosphate buffered saline (PBS), Ringers solution or lactated Ringers injection. The aqueous carrier liquid also may include fixed oils, fatty esters or polyols, particularly if the aqueous mixture for injection is a suspension. The aqueous carrier liquid also may include one or more other substances such as buffers, stabilizers, solubilizers, preservatives and antioxidants. Preferably the solid composition dissolves in the aqueous carrier liquid to form a solution.

Presently preferred aqueous carrier liquids include sodium chloride injection, such as solutions containing 0.9%, 0.45% or 0.225% sodium chloride. Presently preferred aqueous carrier liquids include sterile water for injection. Presently preferred aqueous carrier liquids include bacteriostatic water for injection, which may include, for example, either 0.9% benzyl alcohol or a combination of methylparaben and propylparaben. Presently preferred aqueous carrier liquids include lactated Ringers injection. Preferably the aqueous carrier liquid does not include dextrose.

The amount of aqueous carrier liquid may be sufficient to provide an initial aqueous mixture containing caspofungin acetate at a concentration of 5 milligrams per milliliter (mg/mL) or 7 mg/mL. At these concentrations, it is convenient to provide a 50 mg or 70 mg dose of caspofungin acetate to a patient, such as by dispensing 10 milliliters (mL) of the aqueous mixture into another aqueous liquid to form a final aqueous mixture. While an initial aqueous mixture containing caspofungin acetate at a concentration of 5 or 7 mg/mL may be injected into a patient, the presently recommended procedure includes combining the initial aqueous mixture with another aqueous liquid to form a final aqueous mixture, which is then administered to a patient.

The amount of aqueous carrier liquid may be sufficient to provide a final aqueous mixture containing caspofungin acetate at a concentration of at most 0.5 mg/mL. For example, 10 mL of an initial aqueous mixture containing 5 or 7 mg/mL caspofungin acetate may be combined with 250 mL of an aqueous carrier liquid to provide a final aqueous mixture containing 0.19 mg/mL or 0.27 mg/mL caspofungin acetate (0.192 mg/mL=50 mg/(250 mL+10 mL); 0.269 mg/mL=70 mg/(250 mL+10 mL)). Presently preferred concentrations of caspofungin acetate in a final aqueous mixture for administration to a patient are from 0.05 to 0.5 mg/mL, from 0.1 to 0.4 mg/mL, and from 0.15 to 0.3 mg/mL. Presently preferred concentrations of caspofungin acetate in a final aqueous mixture for administration to a patient include 0.19 mg/mL and 0.27 mg/mL.

An aqueous mixture formed from the solid composition may be administered to provide an initial dose of 50-70 mg of caspofungin acetate to a patient. An aqueous mixture formed from the solid composition may be administered to provide a daily dose of 35-70 mg of caspofungin acetate to a patient. Doses outside of these ranges also may be administered. Typically, an initial dose includes 70 mg caspofungin acetate, and subsequent daily doses include 50 mg/mL caspofungin acetate. Daily doses of 70 mg/mL caspofungin acetate may be advisable under certain conditions, such as an insufficient response by the fungal infection and co-administration with other drugs that induce drug clearance (such as rifampin, nevirapine, efavirenz, carbamazepine, dexamethasone and phenytoin). Daily doses below 50 mg/mL of caspofungin acetate may be advisable under certain conditions, such as for pediatric patients or patients having moderate hepatic impairment.

To provide a clear and more consistent understanding of the specification and claims of this application, the following definitions are provided.

The term "group" means a linked collection of atoms or a single atom within a molecular entity, where a molecular entity is any constitutionally or isotopically distinct atom, molecule, ion, ion pair, radical, radical ion, complex, conformer etc., identifiable as a separately distinguishable entity.

The term "amino acid" means a molecular entity that includes at least one carboxylic acid group [—C(=O)OH] and at least one primary or secondary amine group [—NH$_2$ or —RNH, where —R is a molecular entity other than —H], but lacking a secondary amide group [—C(=O)—NH—].

The term "mass ratio" of two substances means the mass of one substance (S1) relative to the mass of the other substance (S2), where both masses have identical units, expressed as S1:S2.

The term "lyophilizing" means removing from a solution or an emulsion one or more substances having the lowest boiling points by freezing the solution or emulsion and applying a vacuum to the frozen mixture.

The term "solid" means a substance that is not a liquid or a gas. A solid substance may have one of a variety of forms, including a monolithic solid, a powder, a gel or a paste.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A composition, comprising:
    from 10 to 150 mg of caspofungin acetate, and
    arginine, where the mass ratio of the arginine to caspofungin acetate is from 1:1 to 3:1;
    where the composition is a solid.

2. The composition of claim 1, comprising from 25 to 100 mg caspofungin acetate.

3. The composition of claim 1, comprising from 50 to 70 mg caspofungin acetate.

4. The composition of claim 1, where the mass ratio of the arginine to caspofungin acetate is 2:1.

5. A composition, comprising:
    50 mg caspofungin acetate, and
    arginine;
    where the mass ratio of arginine to caspofungin acetate is from 1:1 to 3:1, and
    the composition is a solid.

6. The composition of claim 5, where the mass ratio of arginine to caspofungin acetate is 2:1.

7. A composition, formed by a method comprising:
    forming a liquid mixture comprising
        a solvent,
        from 10 to 150 mg of caspofungin acetate, and
        arginine, where the mass ratio of arginine to caspofungin acetate is from 1:1 to 3:1; and
    lyophilizing the liquid mixture to form a solid composition.

8. The composition of claim 7, comprising from 25 to 100 mg caspofungin acetate.

9. The composition of claim 7, comprising from 50 to 70 mg caspofungin acetate.

10. The composition of claim 7, where the mass ratio of arginine to caspofungin acetate is 2:1.

11. The composition of claim 1, wherein following storage of the composition at 25° C. for a period of 29 days, the amount of total impurities present in the composition is not more than 1.0% as determined by peak area percent using High Pressure Liquid Chromatography.

12. The composition of claim 1, wherein following storage of the composition at 40° C. for a period of 29 days, the amount of total impurities present in the composition is not more than 2.0% as determined by peak area percent using High Pressure Liquid Chromatography.

13. The composition of claim 5, wherein following storage of the composition at 25° C. for a period of 29 days, the amount of total impurities present in the composition is not more than 1.0% as determined by peak area percent using High Pressure Liquid Chromatography.

14. The composition of claim 5, wherein following storage of the composition at 40° C. for a period of 29 days, the amount of total impurities present in the composition is not more than 2.0% as determined by peak area percent using High Pressure Liquid Chromatography.

15. The composition of claim 6, wherein following storage of the composition at 25° C. for a period of 29 days, the amount of total impurities present in the composition is not more than 1.0% as determined by peak area percent using High Pressure Liquid Chromatography.

16. The composition of claim 6, wherein following storage of the composition at 40° C. for a period of 29 days, the amount of total impurities present in the composition is not more than 2.0% as determined by peak area percent using High Pressure Liquid Chromatography.

17. A composition, comprising:
    70 mg caspofungin acetate, and
    arginine;
    where the mass ratio of arginine to caspofungin acetate is from 1:1 to 3:1, and
    the composition is a solid.

18. The composition of claim 17, where the mass ratio of arginine to caspofungin acetate is 2:1.

19. The composition of claim 17, wherein following storage of the composition at 25° C. for a period of 29 days, the amount of total impurities present in the composition is not more than 1.0% as determined by peak area percent using High Pressure Liquid Chromatography.

20. The composition of claim 17, wherein following storage of the composition at 40° C. for a period of 29 days, the amount of total impurities present in the composition is not more than 2.0% as determined by peak area percent using High Pressure Liquid Chromatography.

21. The composition of claim 18, wherein following storage of the composition at 25° C. for a period of 29 days, the amount of total impurities present in the composition is not more than 1.0% as determined by peak area percent using High Pressure Liquid Chromatography.

22. The composition of claim 18, wherein following storage of the composition at 40° C. for a period of 29 days, the amount of total impurities present in the composition is not more than 2.0% as determined by peak area percent using High Pressure Liquid Chromatography.

* * * * *